United States Patent [19]

Fruchey

[11] Patent Number: 4,487,720
[45] Date of Patent: Dec. 11, 1984

[54] SEPARATION AND PRODUCTION OF ORGANIC SATURATED MONOCARBOXYLIC ACIDS

[75] Inventor: Olan S. Fruchey, Corpus Christi, Tex.

[73] Assignee: Celanese Corporation, New York, N.Y.

[21] Appl. No.: 423,899

[22] Filed: Sep. 27, 1982

[51] Int. Cl.³ .............................................. C11C 1/08
[52] U.S. Cl. .................................. 260/419; 260/413; 562/531
[58] Field of Search ............... 562/531; 260/413 R, 260/413 N, 419; 252/413

[56] References Cited

U.S. PATENT DOCUMENTS

| | | | |
|---|---|---|---|
| 1,998,997 | 4/1935 | Tolman | 260/413 R |
| 2,355,140 | 8/1944 | Bludworth | 568/410 X |
| 2,444,399 | 6/1948 | Duval et al. | 562/531 |
| 2,456,549 | 12/1948 | Weisman et al. | 562/531 |
| 2,470,859 | 5/1949 | Pavlic | 562/531 |
| 2,766,267 | 10/1956 | Hill | 260/413 R |
| 2,779,808 | 1/1957 | Whitaker | 562/531 X |
| 3,047,599 | 7/1962 | Büchner et al. | 260/413 N |
| 3,579,575 | 5/1971 | Bouniot | 562/531 |

*Primary Examiner*—Helen M. S. Sneed
*Attorney, Agent, or Firm*—L. I. Grim; M. Turken

[57] ABSTRACT

In the purification of the corresponding acid products obtained by oxidizing $C_5$ to $C_9$ organic saturated aliphatic aldehydes in the presence of a combination of manganese and copper catalysts soluble in said acids, the liquid acid reaction product is separated from the soluble catalysts by distillation in the presence of a sufficient amount of oxygen to prevent copper from plating out on the distillation equipment.

22 Claims, 1 Drawing Figure

SEPARATION AND PRODUCTION OF ORGANIC SATURATED MONOCARBOXYLIC ACIDS

This invention relates to an improved purification process for the separation of organic saturated aliphatic monocarboxylic acids containing from 5 to 9 carbon atoms, produced by oxidation of the corresponding aldehydes, from manganese and copper catalysts soluble in these acids. The separation is carried out by distilling the manganese- and copper-containing acid reaction product in the presence of a sufficient amount of oxygen to prevent copper from plating out on the distillation equipment. This separation procedure renders unnecessary any metals separation step before the acid product can be recovered, and permits recovery of the acid product as well as recycle of the still active catalyst solution and unreacted aldehyde, also recovered by distillation, for further use in the aldehyde oxidation step.

BACKGROUND OF THE INVENTION

When oxidizing organic saturated aliphatic aldehydes containing 5 to 9 carbon atoms to the corresponding monocarboxylic acids, the overall objective is to obtain the highest yields and product efficiencies at the highest conversion levels in a single pass, thereby avoiding recycle of significant amounts of unreacted starting materials. Catalysts comprising copper and manganese facilitate this objective, since they result in the production of larger amounts of acid per pass than do manganese catalysts alone. However, a disadvantage often resulting from the use of copper-manganese catalysts in aldehyde oxidation processes, particularly ones in which the reaction product must be distilled to recover the desired product, is plating out of copper in the distillation apparatus. Plating out, of course, leads to undesirable mechanical problems, including erosion of reboilers and pump impellers and rapid pump seal failures.

Copending U.S. application Ser. No. 345,890 filed Feb. 4, 1982, assigned to Celanese Corporation which is a continuation-in-part of application Ser. No. 340,689 filed Jan. 18, 1982, now abandoned, which in turn is a continuation of application Ser. No. 210,992 filed Nov. 28, 1980, now abandoned, which is a continuation of application Ser. No. 065,241 filed Aug. 8, 1979 describes such a process. This process provides commercially attractive high carbon efficiencies of aldehyde to acid at high aldehyde conversions. A single stage or two stage liquid phase reactor system generally gives sufficiently high aldehyde conversions so that recycle of unreacted aldehyde is, in most cases, unnecessary. However, when the reaction mixture is distilled to recover the acid, copper tends to precipitate and plate out on the distillation apparatus.

One means of overcoming this problem is to add oxalic acid per se to precipitate copper and manganese from the reaction mixture as their oxalates, prior to the distillation step. This process is described in U.S. Pat. No. 4,289,708, issued Sept. 15, 1981 to Scott et al and assigned to Celanese Corporation. Copper and manganese can also be separated from the reaction mixture by precipitating them, again as their oxalates, by adding an aqueous oxalic acid solution. In this case, the manganese and copper oxalates precipitate into the aqueous phase, which can be readily separated from the organic acid product by decantation. The acid can then be further purified by distillation. However, aqueous oxalic acid cannot be used satisfactorily to treat mixtures containing valeric acid due to this acid's high solubility in water. This process is described in U.S. Pat. No. 4,246,185, issued Jan. 20, 1980 to Wood, Jr. and assigned to Celanese Corporation.

Japanese Patent No. 52-33614, published Mar. 14, 1977, describes the use of the catalyst combination of copper and manganese in the oxidation of acetaldehyde to acetic acid.

A paper entitled "Metal-ion Catalyzed Oxidation of Acetaldehyde" p. 363–381 written by G. C. Allen and A. Aguilo for the *Advances in Chemistry Series* 76, published by the American Chemical Society, 1968 in a book entitled *Oxidation of Organic Compounds Volume II (Gas-Phase Oxidations, Homogeneous and Heterogeneous Catalysis Applied Oxidations and Synthetic Processes,* also describes the use of catalysts comprising copper and manganese, and manganese alone, for the oxidation of acetaldehyde to acetic acid. At page 380, this paper states as follows:

"Acetic acid can also be produced by oxidizing acetyl radicals by copper (II); the copper (I) formed could easily be reoxidized by oxygen."

This reoxidation occurs in the reactor or unit and not in the recovery distillation operation.

U.S. Pat. No. 3,361,806, issued Jan. 2, 1968 to Lidov and assigned to Halcon International, Inc. describes the catalytic oxidation of an oil containing cyclohexane, cyclohexanol and other oxygenated products in the presence of manganese alone and manganese with copper.

THE INVENTION

This invention, as stated above, involves simply distilling 5 to 9 carbon atom-containing saturated aliphatic monocarboxylic acids, obtained by oxidizing the corresponding aldehydes using a copper/manganese catalyst, such distillation being carried out in the presence of sufficient oxygen to prevent the copper from plating out on the distillation equipment.

Moreover, it has also been found that if oxygen is used during the distillation of unreacted aldehyde from the aforementioned liquid oxidation reaction products containing copper and manganese catalysts, not only can copper plating be prevented and unreacted aldehyde recovered for recycle to the oxidation step, but the oxidation step itself can also be operated at lower aldehyde conversions and higher acid efficiencies, thus giving improved overall acid yields.

Thus, the invention is further directed to an improved process for producing an organic saturated aliphatic monocarboxylic acid containing 5 to 9 carbon atoms which involves the following steps:

(1) the saturated aldehyde starting material is oxidized to the corresponding acid in the presence of a catalyst which is a combination of manganese and copper compounds soluble in the acid produced;

(2) unreacted aldehyde is separated from the acid product by distillation in the presence of sufficient oxygen in the liquid reaction medium to prevent copper from plating out on the distillation equipment;

(3) the acid product is then separated from the catalyst solution by continuing distillation in the presence of sufficient oxygen to prevent copper from plating out; and (4) unreacted aldehyde and catalyst are recycled to the aldehyde oxidation step.

Included among the acids which can be produced by this process are valeric acid from valeraldehyde, hexanoic acid from hexanal, heptanoic acid from heptanal and nonanoic acid from nonanal. It has been discovered that if the overall conversion of aldehyde to all products by means of the catalytic process of this invention is controlled at levels in the range from about 70 to about 90 percent, preferably in the range from about 70 to about 85 percent, and unreacted aldehydes are recycled for further oxidation, improved acid efficiencies and overall acid yields are obtained as compared to those obtained in a process involving the use of a catalyst comprising copper and manganese or a manganese catalyst alone in a single stage liquid phase oxidation at a level of overall aldehyde conversions greater than 90 percent without recycling the unconverted aldehyde.

An added advantage of using copper and manganese as the oxidation catalyst in the production of n-valeric acid from n-valeraldehyde is that less butyl valerate is produced as a by-product than is produced when manganese alone is used as the catalyst. Butyl valerate boils within 1° C. of valeric acid and forms a 25/75 azeotrope with the acid. Thus, butyl valerate cannot be readily separated from valeric acid by distillation. Using copper and manganese as the catalyst for valeric acid production, thus can yield higher purity valeric acid (e.g., >98.5%) than does manganese alone.

Any copper and manganese compounds soluble in the acids they are producing can be used as the catalyst. The preferred compounds are soluble manganous and cupric salts; the most preferred compounds are manganous acetate and cupric acetate. The amounts of copper and manganese, as the metals, which are generally employed can range from about 10 to about 2000 parts per million each of manganese and copper, and preferably about 200 to about 600 parts per million each of manganese and copper, based on the weight of the liquid reaction medium. The mole ratio of manganese to copper can range from about 5:1 to about 0.5:1, and preferably from about 3:1 to about 1:1.

In a single stage liquid phase process carried out in accordance with the present invention, the reaction can be operated at a pressure in the range from about 20 to about 150 pounds per square inch gauge, and preferably from about 85 to about 90 pounds per square inch gauge, at a temperature in the range from about 50° C. to about 80° C., and preferably at a temperature of from about 55° C. to about 65° C.

In the aldehyde oxidation reaction, air is commonly employed as the source of molecular oxygen, although pure oxygen gas may also be emloyed. Molecular oxygen will be provided in at least a stoichiometrically sufficient amount to convert the aldehyde starting material to the corresponding carboxylic acid and to compensate or allow for by-products such as carbon dioxide. The ratio of total feed of oxygen to total feed of organic starting material is a highly variable number which depends upon the specific compositions of the feed, the desired products, and other process design factors. Typically, oxygen or an oxygen-containing gas is bubbled through the liquid reaction mixture in an amount sufficient to prevent oxygen starvation which may be indicated by a low concentration of oxygen or a high ratio of carbon monoxide to carbon dioxide, or both, in the vent gas.

The oxidation reaction will be conducted in the liquid phase, i.e., the aldehyde to be oxidized is in liquid form. Typically, the carboxylic acid reaction product serves as a solvent in which the reaction takes place. The reaction or reaction residence time may range from about 0.1 to about 5 hours, preferably from about 0.3 to about 1 hour. The residence time is calculated as follows:

$$\text{Residence Time} = \frac{\text{volume of solution in reactor, ml}}{\text{feed rate of aldehyde, ml/hr}}$$

Other conditions and results of the oxidation reaction are calculated as follows:

Oxygen Conversion % =

$$\frac{\text{moles O}_2 \text{ fed} - \text{moles O}_2 \text{ in vent}}{\text{moles O}_2 \text{ fed}} \times 100$$

Aldehyde Accountability % =

$$\frac{\text{moles of aldehyde and equivalent in product}}{\text{moles aldehyde fed}} \times 100$$

Aldehyde Conversion % = $\frac{\text{moles aldehyde converted}}{\text{moles aldehyde fed}} \times 100$ Efficiency to Product % =

$$\frac{\text{moles of product produced}}{\text{moles aldehyde fed-moles unreacted aldehyde}} \times 100$$

Unreacted aldehyde is recovered from the oxygenated reaction mixture using standard distillation means. The recovered aldehyde is generally recycled to the oxidation process. The distillation unit must have sufficient means, i.e., trays, plates, packing, etc., to permit separation of the aldehyde starting material from the acid product. During distillation, a sufficient amount of oxygen is passed through the liquid reaction product to prevent plating of the copper present in the reaction mixture. Due to its high solubility in the reaction mixture, manganese does not plate out as readily as copper and thus does not give rise to a plating out problem. Oxygen can be supplied as air, as the substantially pure gas, or in other combinations with inert gases such as nitrogen. The function of the added oxygen is to keep the copper in an oxidation environment, thus preventing $Cu^+$ reduction which results in copper metal plating. The amount of oxygen required to prevent copper plating is a function of temperature, copper concentration and gas sparging efficiency. The amount of air which can be passed through the liquid reaction product during distillation to prevent plating out of the copper on the distillation equipment, is about 0.005 to about 1.0, preferably about 0.015 to about 0.7 standard cubic feet of air per pound liquid reaction product. It has been discovered that if copper plating has occurred from the liquid reaction mixture, an increase in the oxygen supply will redissolve the copper. An excess of oxygen is not detrimental to the distillation process. However, an excessive amount of oxygen passing through the liquid reaction mixture will require additional energy requirements to maintain the equilibrium of the distillation process.

Any of several distillation procedures can be used in the process of this invention. If the amount of unreacted aldehyde present in the acid reaction product is less than about 5 weight percent of the total product, the acid product together with unreacted aldehyde can be flashed from the catalyst-containing solution. If the amount of unreacted aldehyde is in excess of about 5 weight percent of the total product, the unreacted aldehyde can be initially separated from the acid product containing the catalyst, followed by the separation of the acid product from catalyst solution. In this case, recovered unreacted aldehyde can be recycled to the aldehyde oxidation reactor. In these distillation procedures, oxygen is supplied to the acid reaction product in sufficient amounts to prevent the copper from plating out on the equipment. At the same time, the catalyst is maintained in active form for reuse or recycle to the aldehyde oxidation reactor.

Recycling dissolved catalyst to the oxidation unit reduces significantly the overall amount of catalyst used in producing valeric acid, heptanoic acid and nonanoic acid from the corresponding aldehydes. It also eliminates the necessity of carrying out aqueous separation of the manganese and copper from heptanoic acid, as described in the aforementioned U.S. Pat. No. 4,246,185.

The invention will be understood more fully by reference to the following examples.

EXAMPLES 1–25

These examples describe the liquid phase oxidation of n-valeraldehyde to valeric acid using two different catalyst systems in three types of processing techniques.

One stage operation—n-valeraldehyde was passed only once through the oxidation unit and the acid product was then removed.

Two stage operation—the acid product obtained by one stage operation was used separately as the feed to the oxidation unit to simulate a two stage process.

One stage operation was carried out to give lower overall conversion of aldehyde to all products per pass than in the first stage of the above-described two stage operation. Unreacted aldehyde and recovered catalyst were recycled to the oxidation unit for further reaction at low conversion. In the distillation for the aldehyde recovery, oxygen was added to the distillation unit when copper was present in the product. If manganese was used alone as the catalyst, no oxygen was needed in the distillation process.

The reactor used for these oxidation reactions was a vertical eight foot section of 2-inch diameter steel pipe with a flanged plate attached to the bottom with fittings for feed (air, aldehyde and catalyst) lines. There were multiple product take-off points in the side of this pipe reactor so that the height of roused liquid above the air sparges could be controlled by selection of the take-off point. Reaction liquid was continually pumped via a centrifugal pump from the bottom of the reactor through a heat exchanger and discharged just above the surface of the liquid in the reactor. The reaction temperature was controlled by controlling the cooling water flow to the heat exchanger on the pump around stream.

Product (both liquid and gas) was taken out through a line (¼ inch) in the side of the reactor into a chilled water cooled (10° C.) gas liquid separator. The gases emerged through a chilled water condenser into a pressure regulating motor valve and were then passed through a dry test meter. The liquid products were collected, weighed and analyzed by gas chromatography. The vent gas was analyzed continuously for oxygen with a polargraphic detector and was analyzed periodically (at approximately 15 minute intervals) for CO, $CO_2$, $N_2$ and $O_2$ by gas chromatography. The concentration of n-valeraldehyde and valeric acid in the vent were calculated from the composition of the liquid phase assuming ideal behavior.

The liquid feed was a solution of approximately 90 weight percent n-valeraldehyde, and small amounts of other $C_5$ aldehydes and $C_5$ acids. The catalyst solution was prepared by dissolving (with heat and stirring) enough manganous acetate or a combination of manganous acetate and cupric acid in valeric acid to yield a 3% catalyst concentration. The actual weight of liquid feed and catalyst fed to the reaction system was measured. The air was fed into the reactor through a Hasting's flow meter. Both the Hasting's flow meter and the dry test meter on the vent stream were recalibrated daily with a large soap bubble flow meter.

EXAMPLES 1 AND 2

One Stage n-Valeraldehyde Oxidation to Valeric Acid—Mn Catalyst Alone

The reaction was carried out using the general operating conditions listed in Tables I and IA below, using manganous acetate alone as the catalyst.

TABLE I

|  | Examples 1 and 2 |
|---|---|
| Pressure | 90 psig |
| Roused Level | 4 feet |
| Reactor Diameter | 2 inch |
| Temperature (sparger tip) | 65° C. |
| Temperature (4 ft. level) | 60° C. |
| Air Flow Rate | 18.5 l/min. |
| Air Superficial Velocity | 0.08 ft/sec. |
| Aldehyde Feed Rate | 35 ml/min. |
| Catalyst Feed Rate | 0.5 ml/min. |
| Conversion | 80% |
| $O_2$ in Vent | 2.5 mole % |
| CO in Vent | 0.8 mole % |
| $CO_2$ in Vent | 2.4 mole % |
| Mn Concentration in Reactor | 600 ppm |

TABLE IA

|  | Example 1 | Example 2 |
|---|---|---|
| Aldehyde Feed (g) | 1827 | 1701 |
| Catalyst Feed (g) | 33 | 33.1 |
| Product Obtained (g) | 2092 | 1921 |
| Vent Volume (l) | 947.6 | 943.6 |
| Air Rate (l/min.) | 18.5 | 18.5 |
| Vent Back Pressure (mm Hg) | 41 | 42 |
| Vent Temperature (°C.) | 21 | 21 |
| Run Time (min.) | 60 | 60 |

Analytical data for the feed and products obtained in Examples 1 and 2 are listed below in Table II.

TABLE II

|  | Example 1 | | Example 2 | |
|---|---|---|---|---|
|  | Feed | Product | Feed | Product |
| n-$C_5$Ald (wt %) | 89.4 | 15.5 | 89.4 | 14.8 |
| *b-$C_5$Ald (wt %) | 3.5 | 1.1 | 3.5 | 1.1 |
| n-$C_5$Acid (wt %) | 4.1 | 77.2 | 4.1 | 74.3 |
| *b-$C_5$Acid (wt %) | 1.0 | 2.3 | 1.0 | 2.2 |
| $C_4$Acid (wt %) | 0.3 | 1.6 | 0.3 | 1.5 |
| Butyl Valerate (wt %) | 0.5 | 1.7 | 0.5 | 1.5 |
| Butanol (wt %) | 0.2 | 0.7 | 0.2 | 0.6 |
| Water (wt %) | 0.3 | 1.3 | 0.3 | 1.3 |

*branched

At a conversion level of n-valeraldehyde of 79.9 percent in Examples 1 and 2, efficiencies to valeric acid of 93.9 percent and 93.8 percent were achieved. One experiment was conducted at an aldehyde conversion level of 67% and the efficiency to valeric acid was 97.1%. It should be noted, however, that significant amounts of butyl valerate, which is extremely difficult to separate from valeric acid were produced in these examples. Lesser amounts of this by-product were obtained when copper and manganese were used together as the catalyst, as described in later examples.

EXAMPLES 3-6

Two Stage n-Valeraldehyde Oxidation to Valeric Acid—Mn Catalyst Alone

The products of Examples 1 and 2 were composited and fed to the same reactor under the conditions described in Tables III and IIIA below.

TABLE III

|  | Examples 3 to 6 |
|---|---|
| Pressure | 90 psig |
| Roused Level | 4 feet |
| Reactor Diameter | 2 inch |
| Temperature (sparger tip) | 55° C. |
| Temperature (4 ft. level) | 50° C. |
| Air Flow Rate | 10.5 l/min. |
| Air Superficial Velocity | 0.04 ft/sec. |
| Feed Rate | 75 ml/min. |
| Conversion (Total) | 96.5% |
| $O_2$ in Vent | 3.9 mole % |
| CO in Vent | 3.0 mole % |
| $CO_2$ in Vent | 0.3 mole % |
| Mn Concentration in Reactor | 600 ppm |

TABLE IIIA

|  | Example 3 | Example 4 | Example 5 | Example 6 |
|---|---|---|---|---|
| Feed (g) | 1678 | 1892 | 1898 | 1919 |
| Product Obtained (g) | 1721 | 1936 | 1952 | 1961 |
| Vent Volume (l) | 259.2 | 255.1 | 260.1 | 260.5 |
| Air Rate (l/min.) | 10 | 10 | 10 | 10 |
| Vent Back Pressure (mm Hg) | 16 | 16 | 16 | 16 |
| Vent Temperature (°C.) | 22 | 22 | 22 | 22 |
| Run Time (min.) | 30 | 30.5 | 30 | 30 |

Analytical data for the feed used and products obtained in Examples 3 through 6 are listed in Table IV.

TABLE IV

ANALYTICAL DATA FOR SECOND STAGE OF THE TWO STAGE SYSTEM (Mn ONLY)

| Analysis | Example 3 | | Example 4 | | Example 5 | | Example 6 | |
|---|---|---|---|---|---|---|---|---|
|  | Feed | Product | Feed | Product | Feed | Product | Feed | Product |
| n-$C_5$ Ald (wt %) | 16.5 | 2.6 | 16.5 | 3.0 | 16.5 | 3.0 | 16.5 | 3.0 |
| *b-$C_5$ Ald (wt %) | 1.4 | 0.6 | 1.4 | 0.3 | 1.4 | 0.2 | 1.4 | 0.2 |
| n-$C_5$ Acid (wt %) | 79.2 | 85.3 | 79.2 | 82.8 | 79.2 | 83.7 | 79.2 | 85.1 |
| *b-$C_5$ Acid (wt %) | 2.4 | 2.8 | 2.4 | 2.7 | 2.4 | 2.7 | 2.4 | 2.8 |
| $C_4$ Acid (wt %) | 2.0 | 3.4 | 2.0 | 3.2 | 2.0 | 3.2 | 2.0 | 3.2 |
| Butyl valerate (wt %) | 1.2 | 1.6 | 1.2 | 1.4 | 1.2 | 1.6 | 1.2 | 1.5 |
| Butanol (wt %) | 0.1 | 0.1 | 0.1 | 0.1 | 0.1 | 0.1 | 0.1 | 0.1 |
| Water (wt %) | 1.3 | 2.1 | 1.3 | 2.1 | 1.3 | 2.1 | 1.3 | 2.1 |
| Aldehyde Overall Conversion % |  | 96.2 |  | 96.1 |  | 96.2 |  | 96.2 |
| Efficiency to Valeric Acid % |  | 83.6 |  | 85.7 |  | 84.7 |  | 85.9 |

*branched

EXAMPLES 7-13

One Stage n-Valeraldehyde Oxidation to Valeric Acid—Cu/Mn 90% Conversions

The catalyst solution used in these examples of one stage operation was prepared by dissolving enough cupric acetate and manganous acetate in valeric acid to yield a solution containing 1.5 weight percent copper and 1.5 weight percent manganese. The operating conditions listed in Tables V and VA below were used.

TABLE V

|  | Examples 7 to 13 |
|---|---|
| Pressure | 90 psig |
| Roused Level | 4 feet |
| Reactor Diameter | 2 inch |
| Temperature (sparger tip) | 60° C. |
| Temperature (4 ft. level) | 50° C. |
| Air Flow Rate | 20 l/min. |
| Air Superficial Velocity | 0.08 ft/sec. |
| Aldehyde Feed Rate | 35 ml/min. |
| Catalyst Feed Rate | 0.6 ml/min. |
| Conversion | 90% |
| $O_2$ in Vent | 2.5% (mole) |
| CO in Vent | 0.2% (mole) |
| $CO_2$ in Vent | 2.0% (mole) |
| Cu/Mn Concentration in Reactor | 300 ppm each |

TABLE VA

DATA FOR FIRST STAGE OXIDATION OF n-VALERALDEHYDE USING Cu/Mn CATALYST

|  | Example 7 | Example 8 | Example 9 | Example 10 | Example 11 | Example 12 | Example 13 |
|---|---|---|---|---|---|---|---|
| Aldehyde feed (g) | 1652 | 1647 | 1565 | 1583 | 1557 | 1181 | 1545 |
| Catalyst fed (g) | 35.4 | 35.7 | 35.8 | 35.6 | 35.7 | 26.8 | 35.6 |
| Product Obtained (g) | 1910 | 1922 | 1843 | 1853 | 1846 | 1389 | 1825 |
| Vent Volume (l) | 942 | 901 | 956 | 943 | 963 | 724 | 945 |
| Air Rate (l/min) | 20 | 20 | 20.75 | 20.5 | 20.5 | 20.5 | 20.5 |
| Vent Back Pressure (mm Hg) | 55 | 57 | 57 | 58 | 65 | 65 | 60 |
| Vent Temperature (°C.) | 25 | 27 | 27 | 26 | 24 | 24 | 26 |
| Run Time (min) | 60 | 60 | 60 | 60 | 45 | 45 | 60 |

Analytical data for the feed used and product obtained in Examples 7-13 are listed in Table VI.

TABLE VI
ANALYTICAL DATA FOR FIRST STAGE OXIDATION OF n-VALERALDEHYDE USING Cu/Mn CATALYST

| Analysis | Example 7 Feed | Example 7 Product | Example 8 Feed | Example 8 Product | Example 9 Feed | Example 9 Product | Example 10 Feed | Example 10 Product | Example 11 Feed | Example 11 Product | Example 12 Feed | Example 12 Product | Example 13 Feed | Example 13 Product |
|---|---|---|---|---|---|---|---|---|---|---|---|---|---|---|
| n-C$_5$ Ald (wt %) | 90.6 | 8.8 | 90.6 | 6.1 | 90.6 | 7.4 | 90.6 | 7.1 | 88.8 | 6.4 | 88.8 | 5.7 | 88.8 | 5.8 |
| *b-C$_5$ Ald (wt %) | 5.0 | 0.5 | 5.0 | 0.8 | 5.0 | 0.5 | 5.0 | 0.4 | 5.0 | 0.4 | 5.0 | 0.8 | 5.0 | 0.8 |
| n-C$_5$ Acid (wt %) | 2.0 | 78.2 | 2.0 | 84.0 | 2.0 | 82.9 | 2.0 | 81.7 | 3.3 | 83.6 | 3.3 | 84.0 | 3.3 | 83.5 |
| *b-C$_5$ Acid (wt %) | 0.2 | 4.2 | 0.2 | 3.3 | 0.2 | 3.2 | 0.2 | 3.5 | 0.3 | 3.3 | 0.3 | 3.2 | 0.3 | 3.3 |
| C$_4$ Acid (wt %) | 0.03 | 2.5 | 0.03 | 3.0 | 0.03 | 2.6 | 0.03 | 2.8 | 0.04 | 2.9 | 0.04 | 3.2 | 0.04 | 3.0 |
| Butyl valerate (wt %) | — | 0.3 | — | 0.3 | — | 0.3 | — | 0.3 | — | 0.3 | — | 0.3 | — | 0.3 |
| Butanol (wt %) | — | 0.2 | — | — | — | 0.2 | — | 0.2 | — | 0.2 | — | 0.3 | — | 0.2 |
| Water (wt %) | 0.3 | 1.4 | 0.3 | 1.4 | 0.3 | 1.5 | 0.3 | 1.7 | 0.3 | 1.7 | 0.3 | 1.9 | 0.3 | 1.9 |
| Cu (ppm) | — | 226 | — | 226 | — | 226 | — | 226 | — | 226 | — | 226 | — | 226 |
| Mn (ppm) | — | 223 | — | 223 | — | 223 | — | 223 | — | 223 | — | 223 | — | 223 |
| Aldehyde Conversion % | 88.3 | | 91.5 | | 90.3 | | 90.5 | | 91.5 | | 91.9 | | 91.5 | |
| Efficiency to Valeric Acid % | 95.5 | | 95.4 | | 95.3 | | 95.2 | | 94.9 | | 94.5 | | 94.8 | |

*branched

An additional run was conducted at a conversion level of 88% n-valeraldehyde to valeric acid and the carbon efficiency to valeric acid was 95.1%.

EXAMPLES 14–18

Two Stage n-Valeraldehyde to Valeric Acid Cu/Mn

The products of Examples 7–13 were composited and fed to the same reactor under the conditions in Tables VII and VIIA described below.

TABLE VII
Examples 14–18

| | |
|---|---|
| Pressure | 90 psig |
| Roused Level | 100 cm |
| Reactor Diameter | 2 inch |
| Temperature (sparger tip) | 60° C. |
| Temperature (100 cm level) | 55° C. |
| Air Flow Rate | 8.5 l/min. |
| Air Superficial Velocity | 0.04 ft/sec. |
| Feed Rate | 100 ml/min. |
| Conversion (Total) | 98.5% |
| O$_2$ in Vent | 3.0% (mole) |
| CO$_2$ in Vent | 4.5% (mole) |
| CO in Vent | 0.1% (mole) |
| Cu/Mn Concentration in Reactor | 300 ppm each |

TABLE VIIA

| | Ex. 14 | Ex. 15 | Ex. 16 | Ex. 17 | Ex. 18 |
|---|---|---|---|---|---|
| Feed (g) | 2243 | 2183 | 2145 | 1483 | 2614 |
| Product Obtained (g) | 2289 | 2227 | 2175 | 1508 | 2656 |
| Vent Volume (l) | 186 | 190 | 143 | 108 | 168 |
| Air Rate (l/min) | 7.5 | 7.5 | 7.5 | 7.5 | 7.5 |
| Vent Back Pressure (mm Hg) | 38 | 38 | 62 | 62 | 42 |
| Vent Temperature (°C.) | 24 | 24 | 26 | 26 | 26 |
| Run Time (min) | 30 | 30 | 30 | 21 | 30 |

Analytical data for the feed used and product obtained in Examples 14–18 are described in Table VIII.

TABLE VIII
ANALYTICAL DATA FOR SECOND STAGE OXIDATION OF THE TWO STAGE SYSTEM (Cu/Mn)

| Analysis | Example 14 Feed | Example 14 Product | Example 15 Feed | Example 15 Product | Example 16 Feed | Example 16 Product | Example 17 Feed | Example 17 Product | Example 18 Feed | Example 18 Product |
|---|---|---|---|---|---|---|---|---|---|---|
| n-C$_5$ Ald (wt %) | 9.1 | 1.2 | 9.1 | 1.0 | 4.6 | 0.6 | 4.6 | 0.5 | 5.9 | 0.6 |
| *b-C$_5$ Ald (wt %) | 0.6 | 0.7 | 0.6 | 0.9 | 0.4 | 0.6 | 0.4 | 0.7 | 0.5 | 0.6 |
| n-C$_5$ Acid (wt %) | 83.3 | 89.7 | 83.3 | 89.5 | 85.4 | 88.2 | 85.4 | 87.9 | 86.2 | 88.1 |
| *b-C$_5$ Acid (wt %) | 3.2 | 3.4 | 3.2 | 8.4 | 3.3 | 3.4 | 3.3 | 3.4 | 3.6 | 3.4 |
| C$_4$ Acid (wt %) | 2.7 | 3.7 | 2.7 | 3.6 | 2.9 | 4.0 | 2.9 | 4.0 | 2.7 | 3.9 |
| Butyl valerate (wt %) | 0.4 | 0.4 | 0.4 | 0.4 | 0.4 | 0.4 | 0.4 | 0.4 | 0.5 | 0.4 |
| Butanol (wt %) | 0.1 | 0.1 | 0.1 | 0.1 | 0.2 | 0.2 | 0.2 | 0.2 | 0.1 | 0.2 |
| Water (wt %) | 1.7 | 2.1 | 1.7 | 2.2 | 1.7 | 2.2 | 1.7 | 2.2 | 1.9 | 2.1 |
| Cu (ppm) | 226 | 216 | 226 | 212 | 220 | 222 | 220 | 217 | 224 | 218 |
| Mn (ppm) | 223 | 224 | 223 | 219 | 217 | 220 | 217 | 226 | 220 | 222 |
| Aldehyde Overall Conversion % | 97.6 | | 97.6 | | 98.5 | | 98.5 | | 98.5 | |
| Overall Efficiency to Valeric Acid % | 90.1 | | 86.4 | | 71.7 | | 69.7 | | 75.7 | |

*branched

EXAMPLES 19–21

One Stage n-Valeraldehyde to Valeric Acid "Low Conversion" Aldehyde and Catalyst Recycle The one stage oxidation unit used in Examples 1 and 2 was set up to permit the recycle of recovered unreacted aldehyde and catalysts. These examples represent a low conversion (70–78%) of n-valeraldehyde to maximize the efficiency to valeric acid. The catalyst copper acetate and manganous acetate was added in the same manner as in Examples 14–18. The reaction conditions used are described in Tables IX and IXA below:

TABLE IX

| | Examples 19–21 |
|---|---|
| Pressure | 90 psig |

TABLE IX-continued

| | Examples 19-21 |
|---|---|
| Roused Level | 4 feet |
| Reaction Diameter | 2 inch |
| Temperature (sparger tip) | 60° C. |
| Temperature (4 ft. level) | 50° C. |
| Air Flow Rate | 12.5 l/min. |
| Aldehyde Feed Rate | 37 ml/min. |
| Catalyst Feed Rate | 3.5 ml/min. |
| Conversion | 70-78% |
| Oxygen in Vent | 2% (mole) |
| CO in Vent | 0.3% (mole) |
| $CO_2$ in Vent | 1.5% (mole) |
| Air Superficial Velocity | 0.06 ft/sec. |
| Cu/Mn Concentration in Reactor | 300 ppm each |

TABLE IXA

| | Example 19 | Example 20 | Example 21 |
|---|---|---|---|
| Aldehyde fed (g) | 1907 | 1728 | 1675 |
| Catalyst fed (g) | 41 | 210 | 210 |
| Product Obtained (g) | 2084 | 2065 | 2098 |
| Vent Volume (l) | 795.2 | 383.75 | 368.3 |
| Air Rate (l/min) | 17.25 | 12.5 | 12.5 |
| Vent Back Pressure (mm Hg) | 40 | 42 | 50 |
| Vent Temperature (°C.) | 27 | 28 | 29 |
| Run Time (min) | 60 | 60 | 60 |

Analytical data for the feed used and product obtained in Examples 19-21 are described in Table X.

TABLE X
ANALYTICAL DATA FOR ONE STAGE OXIDATION REACTOR (Cu/Mn)

| | Example 19 | | Example 20 | | Example 21 | |
|---|---|---|---|---|---|---|
| Analysis | Feed | Product | Feed | Product | Feed | Product |
| n-$C_5$ Ald (wt %) | 90.0 | 18.1 | 90.0 | 20.9 | 90.8 | 21.9 |
| *b-$C_5$ Ald (wt %) | 4.9 | 1.5 | 4.9 | 1.2 | 4.3 | 1.5 |
| n-$C_5$ Acid (wt %) | 3.4 | 71.3 | 3.4 | 70.2 | 2.0 | 70.4 |
| *b-$C_5$ Acid (wt %) | 0.3 | 2.7 | 0.3 | 2.8 | 0.2 | 2.8 |
| $C_4$ Acid (wt %) | 0.1 | 1.2 | 0.1 | 1.2 | 0.1 | 1.0 |
| Water (wt %) | 0.3 | 1.0 | 0.3 | 1.0 | 0.3 | 0.9 |
| Butyl valerate (wt %) | — | 0.2 | — | 0.3 | — | 0.2 |
| Butanol (wt %) | — | 0.2 | — | 0.2 | — | 0.2 |
| Cu (ppm) | — | 257.0 | — | 290.0 | — | 255.0 |
| Mn (ppm) | — | 237.0 | — | 273.0 | — | 240.0 |
| Aldehyde Conversion % | 75.1 | | 71.8 | | 69.5 | |
| Overall Efficiency | 97.4 | | 97.3 | | 97.4 | |
| to Valeric Acid % | | | | | | |

*branched

An additional run was conducted at a conversion level of 78% n-valeraldehyde to valeric acid and a carbon efficiency to valeric acid of 98.6%.

Table XI summarizes the results of the runs reported in Examples 1 through 21. The figures given for overall aldehyde conversion and acid efficiency are the numerical averages of the runs carried out in each type of process, and are reported at 95% confidence level. The yields of valeric acid in the one stage processes or the first stage of the two stage process are calculated by multiplying the determined acid efficiencies obtained by the aldehyde conversion level. In the two stage process, Examples 3-6 and 14-18, the product from the first stage was passed through a second stage to convert further the unreacted aldehydes. The average efficiencies were determined for each set of runs and the range of yields calculated from the data. In Examples 19-21, the conversion of aldehyde was controlled at 69.5-75.1 percent, with the remainder of the unreacted aldehyde recycled at a 98% efficiency as illustrated in Examples 22 and 23. The highest aldehyde efficiencies and yields were obtained in the one stage process with unreacted aldehyde and catalyst recycle.

TABLE XI
SUMMARY OF RESULTS OF EXAMPLES 1-21

| Examples | Number of Stages | Catalyst System | Oxidation Stage | Overall[a] Aldehyde Conversion Wt % | Aldehyde Efficiency[b][c] to Acid % | Yields Valeric Acid % |
|---|---|---|---|---|---|---|
| 1 and 2 | 1 | Mn | First | 80 | 93.9 ± .05 | 74.7-75.5 |
| 3-6 | 2 | Mn | Second | 96 | 85.0 ± 2.5 | 87.7-89.5 (overall of 1st & 2nd stages) |
| 7-13 | 1 | Cu/Mn | First | 90 | 95.0 ± 0.6 | 85.0-85.9 |
| 14-18 | 2 | Cu/Mn | Second | 98.1 | 72.4 ± 8.9 | 90.5-92.5 (overall of 1st & 2nd stages) |
| 19-21 | 1 | Cu/Mn | First (with 98% efficiency aldehyde recycle) | 74 | 97.6 ± 1.5 | 94.2-97.9 (98% efficiency aldehyde recycle) |

[a]numerical averages of runs
[b]numerical averages of runs
[c]ranges are at 95% confidence level

EXAMPLES 22-23

The products of Examples 19-21 were composited and divided into two portions to recover unreacted aldehyde, acid product and catalyst.

The aldehyde recycle column was a 2 inch, 20 tray Oldershaw column with feed at tray 10 and an air bleed of 0.5 standard cubic feet per hour per pound reboiler liquid in the bottom of the reboiler. The operating conditions used are given in Table XII below:

TABLE XII

| | Examples 22-23 |
|---|---|
| Overhead Pressure | 200 mm Hg |
| Trays | 20 |

The aldehyde data for the aldehyde recycle column are listed in Table XIV.

TABLE XIV
ANALYTICAL DATA FOR ONE STAGE OXIDATION ALDEHYDE RECYCLE COLUMN (Cu/Mn)

| | Example 22 | | | | Example 23 | | | |
|---|---|---|---|---|---|---|---|---|
| | | | Overhead | | | | Overhead | |
| Analysis[a] | Feed | Base | Organic | Aqueous | Feed | Base | Organic | Aqueous |
| n-$C_5$ Ald (wt %) | 21.0 | 0.5 | 83.8 | 2.0 | 21.0 | 0.5 | 85.8 | 1.9 |
| *b-$C_5$ Ald (wt %) | 0.9 | 0.1 | 4.5 | 0.4 | 0.9 | 0.1 | 5.2 | 0.4 |
| n-$C_5$ Acid (wt %) | 71.3 | 84.5 | 3.5 | — | 71.3 | 89.5 | 3.5 | — |
| *b-$C_5$ Acid (wt %) | 2.7 | 3.8 | 0.4 | — | 2.7 | 3.6 | 0.3 | — |
| $C_4$ Acid (wt %) | 1.1 | 1.6 | 0.4 | — | 1.1 | 1.4 | 0.2 | — |
| Aldol[b] (wt %) | ND | ND | ND | ND | ND | ND | ND | ND |
| Water (wt %) | 1.2 | 0.01 | 2.3 | 97.5 | 1.2 | 0.01 | 2.3 | 97.5 |
| Butyl valerate (wt %) | 0.2 | 0.4 | 0.1 | — | 0.2 | 0.6 | 0.03 | — |
| Butanol (wt %) | 0.2 | 0.02 | 0.7 | — | 0.2 | 0.02 | 0.6 | — |
| Cu (ppm) | 243 | 336 | — | — | 243 | 370 | — | — |
| Mn (ppm) | 236 | 320 | — | — | 236 | 342 | — | — |

*branched
[a] Ketones and olefin oxides were not specifically looked for during these runs. However, no unidentified peaks were present in amounts >0.5%.
[b] The aldol product of valeraldehyde was not detected (ND).

| | Examples 22–23 |
|---|---|
| Feed Tray | 10 |
| Temperature (Base) | 140° C. |
| Temperature (Tray 10) | 80° C. |
| Temperature (Feed) | 75° C. |
| Temperature (Overhead) | 80° C. |
| Temperature (Reflux) | 75° C. |
| Feed Rate | 40 ml/min. |
| Base Take-Off Rate | 30 ml/min. |
| Overhead Take-Off Rate | 10 ml/min. |
| Reflux Rate | 40 ml/min. |
| Air Bleed Rate | 0.5 SCFH |
| Aldehyde in Base | 0.5% |
| Acid in Overhead | Approximately 1.0% |

The aldehyde, together with water formed in the oxidation reaction, were taken overhead and phase separated. No copper plated in the distillation column while air was bled into the liquid being distilled. The overhead aldehyde stream was recycled to the oxidation unit while the base (which contained <0.5 weight percent aldehyde) was fed to the flasher which readily separates the product from the catalyst by rapid volatilization. The mass balance data for the aldehyde recycle column are listed as follows in Table XIIA.

TABLE XIIA

| | Example 22 | Example 23 |
|---|---|---|
| Feed (g) | 1813 | 1846 |
| Base (g) | 1407 | 1410 |
| Organic Overhead (g) | 423 | 420 |
| Water Overhead (g) | 19 | 25 |
| Elapsed Time (min.) | 52 | 53 |
| Accountability (%) | 102 | 100.5 |

Aldehyde column recycle efficiency data are listed in Table XIII.

TABLE XIII

| | Example 22 | Example 23 |
|---|---|---|
| Feed Weight (g) | 1813 | 1846 |
| Aldehyde Content in Feed (%) | 21.9 | 21.9 |
| Aldehyde in Feed (g) | 397 | 404 |
| Base Weight (g) | 1407 | 1410 |
| Aldehyde Content in Base (%) | 0.5 | 0.5 |
| Aldehyde in Base (g) | 7 | 7 |
| Percent Aldehyde not Recycled (%) | 2 | 2 |
| Aldehyde Recycle Eff. (%) | 98[a] | 98[a] |

[a] The aldehyde recycle efficiency was obtained by substracting the percent aldehyde not recycled from 100%.

The above data indicate that the aldehyde recycle efficiency to the oxidation reactor is 98 percent and no aldol product was detected in any of the streams. The aldehyde was recycled 10 times with no apparent problems during the course of the one stage aldehyde oxidation operation using the copper and manganese catalyst combination.

EXAMPLES 24–25

The copper and manganese catalyst was removed from the aldehyde column base product as described in Examples 22 and 23 via flashing under mild operating conditions, given in Table XV below.

TABLE XV

| | Examples 24–25 |
|---|---|
| Overhead Pressure | 90 mm Hg |
| Temperature (Base) | 135° C. |
| Temperature (Reboiler Skin) | 158° C. |
| Temperature (Feed) | 100° C. |
| Temperature (Overhead) | 127° C. |
| Feed Rate | 30 ml/min. |
| Base Take-Off Rate | 3.5 ml/min. |
| Overhead Take-Off Rate | 26.5 ml/min. |
| Air Bleed Rate | 0.5 SCFH |
| Cu/Mn in Base | 3000 ppm each |
| Cu/Mn in Overhead | <1 ppm each |

The raw mass balance data for the one stage oxidation flasher system (Cu/Mn) are listed in Table XVA.

TABLE XVA

| | Example 24 | Example 25 |
|---|---|---|
| Feed (g) | 1320 | 1924 |
| Overhead (g) | 1218 | 1149 |
| Base (g) | 156 | 161 |
| Elapsed Time (min.) | 45 | 50 |
| Accountability (%) | 104 | 101 |

An air bleed (0.5 standard cubic feet per hour per pound reboiler liquid) was required to prevent copper plating. If no air was bled into the liquid product being distilled, copper would plate on the distillation equipment. The copper-manganese concentration in the overhead product was <1 part per million each of copper and manganese. Analytical data for the flasher system are shown in Table XVI below.

TABLE XVI

| Analysis | Example 24 | | | Example 25 | | |
|---|---|---|---|---|---|---|
| | Feed | Base | Overhead | Feed | Base | Overhead |
| n-C$_5$Ald (wt %) | 0.4 | — | 0.3 | 0.4 | — | 0.3 |
| *b-C$_5$Ald (wt %) | — | — | — | — | — | — |
| n-C$_5$Acid (wt %) | 90.3 | 84.1 | 90.8 | 90.3 | 90.1 | 89.2 |
| *b-C$_5$Acid (wt %) | 3.3 | 2.4 | 3.5 | 3.3 | 2.4 | 3.5 |
| C$_4$Acid (wt %) | 1.3 | 0.8 | 1.5 | 1.3 | 0.9 | 1.5 |
| Water (wt %) | 0.01 | — | 0.01 | 0.01 | — | 0.01 |
| Butanol (wt %) | — | — | — | — | — | — |
| Butyl Valerate (wt %) | 0.3 | 0.2 | 0.4 | 0.3 | 0.4 | 0.6 |
| Cu (ppm) | 365 | 2770 | <1 | 365 | 3170 | <1 |
| Mn (ppm) | 351 | 2650 | <1 | 341 | 3000 | <1 |

*branched

The catalyst solution recovered in this process was recycled to oxidation unit fifteen times in the operation of the one stage oxidation "low conversion" of valeraldehyde to valeric acid.

In order to illustrate more certain embodiments of this invention, reference is made to the drawing, which schematically depicts a process flow diagram of a preferred embodiment of this invention for heptanoic and nonanoic acid production.

Air is transmitted via a line 1 to an oxidation reactor 2 having a vent 9. The reactor 2 contains heptanal, fed through a line 3 (fresh heptanal) and a line 4 (recycled heptanal), and cupric acetate and manganous acetate, fed through line 5 (fresh catalyst) and line 6 (recycled catalyst). The reaction product from the oxidation reactor 2 is sent via line 7 to an aldehyde distillation tower 8 containing an air feed 10. The aldehyde (heptanal) produced is separated from the acid reaction product by distillation and the catalyst-acid product is passed via line 11 to a surge tank 12. Aldehyde is distilled overhead via line 13 to an aldehyde-water decantation unit 14 containing a vent 15 and water removal line 16. The decanted unreacted aldehyde is passed via line 17, wherein part of the aldehyde can be used as overhead reflux through line 18 in the aldehyde distillation tower 8 and the remainder can be recycled, through line 4, to the oxidation reactor 2. The catalyst-acid product in the surge tank 12 is passed via line 19 to the catalyst vacuum flasher 20, into which air is also fed through line 21.

The catalyst is separated from the acid product by distillation in a catalyst vacuum flasher 20. A catalyst solution containing heptanoic acid is recycled via line 22 to surge tank 23, then continuing through line 6 back to the oxidation reactor 2. The acid product is distilled overhead via line 24 and passed into the heavy ends distillation tower 25 wherein the heavy ends residue is removed through line 27 and the acid product distilled overhead is passed through line 26 to the finishing distillation tower 28 containing vent 29, air feed 31, a vapor side stream take off 30 for the finished acid product. The acid residue product is passed through line 32 back to the heavy ends distillation tower for further purification.

The following example illustrates a continuous process for the production of heptanoic acid carried out in accordance with the process of the present invention in equipment of the type shown in the drawing.

The following oxidation reactor conditions were used:

| 316 Stainless Steel | |
|---|---|
| Dimensions | |
| Height | 4.57 meters |
| Diameter | 20.3 centimeters |
| Pressure | 88 psig |
| Unroused Liquid Level | 1.5 meters |
| Temperatures | |
| Air sparger tip (not shown in drawing) | 55° C. |
| Middle of liquid | 55° C. |
| Top of liquid | 55° C. |
| Vapor space | 53° C. |
| Vent | 25° C. |
| Vent Back Pressure | 2 psig |
| Catalyst Concentrations | |
| Copper | 280 parts per million |
| Manganese | 300 parts per million |
| Vent Gas Concentrations | |
| O$_2$ | 3.85 mol % |
| CO | 0.53 mol % |
| CO$_2$ | 1.26 mol % |
| Flow Rates | |
| Fresh aldehyde | 17 kilograms/hour |
| Recycle aldehyde | 7.3 kilograms/hour |
| Catalyst | 2.75 kilograms/hour |
| Air | 9600 standard liter/hour |
| Reactants recirculation in reactor | 2500 kilograms/hour |
| Product | 29 kilograms/hour |
| Vent | 10.4 kilograms/hour |

| | Fresh Aldehyde Feed Composition Wt % |
|---|---|
| Hexene + Hexane | 0.15 |
| 2-methyl hexanal | 5.9 |
| Heptanal | 93.73 |
| Hexanoic acid | — |
| 2-methyl hexanoic acid | 0.01 |
| Heptanoic acid | 0.21 |
| Hexyl hexanoate ester | — |
| Hexyl heptanoate ester | — |
| Heptyl heptanoate ester | — |
| Water | — |
| Heptanoic/anhydride | — |

The oxidation reaction product was sent to the aldehyde reaction recycle distillation tower operated under the following conditions:

| 316 Stainless Steel Tower - Dimensions | |
|---|---|
| Height | 6.1 meters |
| Diameter | 15.2 centimeters |
| Feed Point | 1.83 meters from bottom of packing |
| Amount of Packing | 4.92 meters (height) |
| Type of Packing | ⅜" 316 stainless steel Pall rings |
| Air Injection Point | Base of reboiler |
| Reboiler Type | Shell-Tube thermosiphon |
| Maximum pressure | 150 millimeters mercury absolute |
| Temperatures | |
| Feed | 100° C. |
| Base | 175° C. |
| Middle | 99° C. |
| Top | 92° C. |
| Reflux | 25° C. |
| Flow Rates | |
| Feed | 29 kilograms/hour |
| Air Feed | 180 standard liters/hour |
| Overhead (recycle aldehyde) | 7.3 kilograms/hour |
| Overhead Water Decant | 0.43 kilogram/hour |
| Residue | 21.25 kilograms/hour |
| Vacuum Vent | 0.82 kilogram/hour |

| 316 Stainless Steel Tower - Dimensions | |
|---|---|
| Reflux | 31.5 kilograms/hour |

The pressure of air flowing through the liquid product being distilled prevents the copper present from plating out onto the distillation equipment. The catalyst acid product was fed through a surge tank which in turn pumped the catalyst acid product to the catalyst vacuum flasher.

The 316 stainless steel catalyst vacuum flasher was operated under the following conditions:

| Dimensions | |
|---|---|
| Height - upper section | 2 meters |
| lower section | 1.7 meters |
| Diameter - upper section | 15.2 centimeters |
| lower section | 7.6 centimeters |
| Feed Point | 2.3 meters from base |
| Water Injection Point | Reboiler inlet |
| Reboiler Type | Shell-Tube Forced |
| Maximum Pressure | 80 millimeters mercury absolute |
| Temperatures | |
| Feed | 50° C. |
| Base | 161° C. |
| Overhead Vapor | 156° C. |
| Flow Rates | |
| Feed | 21 kilograms/hour |
| Air Feed | 180 standard liters/hour |
| Water Feed | 0.30 kilogram/hour |
| Overhead (heavy ends feed) | 18.6 kilograms/hour |
| Residue (catalyst recycle) | 2.4 kilograms/hour |
| Catalyst to Oxidation Reactor Blow Down | 0.69 kilogram/hour |

| | Catalyst Recycle Composition Wt % |
|---|---|
| Hexyl hexanoate ester | 0.3 |
| Hexyl heptanoate ester | 3.0 |
| Heptyl heptanoate ester | 1.71 |
| 2-methyl hexanoic acid | 3.0 |
| Heptanoic acid | 43.78 |
| Aldol | 3.13 |
| Heptanoic anhydride | 4.03 |
| Other heavy ends | 41.05 |
| Copper - parts per million | 4284 |
| Manganese - parts per million | 4837 |

The acid product or overhead stream is passed into the 316 stainless steel heavy ends distillation tower operated under the following conditions:

| Dimensions | |
|---|---|
| Height | 15.2 meters |
| Diameter | 20.3 centimeters |
| Feed Point | 9.5 meters from bottom packing |
| Amount of Packing | 15.2 meters |
| Type of Packing | 1" 316 stainless steel Pall rings |
| Acid Recycle Entry Point | 10.2 meters from base |
| Reboiler Type | Shell-Tube Forced |
| Maximum Pressure | 60 millimeters mercury absolute |
| Temperatures | |
| Base | 215° C. |
| Middle | 170° C. |
| Top | 150° C. |
| Reflux | 27° C. |
| Feed (vapor) | 156° C. |
| Flow Rates | |
| Feed | 18.6 kilograms/hour |
| Acid Recycle Feed (from finishing tower 33) | 4.8 kilograms/hour |
| Overhead (finishing feed 25) | 22.9 kilograms/hour |
| Overhead Water Decant | 0 |
| Heavy ends residue blowdown | 0.51 kilogram/hour |
| Reflux | 53 kilograms/hour |
| Vacuum Vent | 0.64 kilogram/hour |

| | Heavy Ends Residue Composition Wt % |
|---|---|
| Hexyl hexanoate ester | 1.0 |
| Hexyl heptanoate ester | 35.36 |
| Heptyl heptanoate ester | 22.41 |
| 2-methyl hexanoic acid | 0.2 |
| Heptanoic acid | 4.8 |
| Aldol | 1.86 |
| Trimer | 0.84 |
| Heptanoic anhydride | 0.1 |
| Other heavy ends | 23.43 |
| Copper - part per million | 4 |
| Manganese - parts per million | 26 |

The overhead acid product of the heavy ends distillation tower is passed to the 316 stainless steel finishing distillation tower operated under the following conditions:

| Dimensions | |
|---|---|
| Height | 18.3 meters |
| Diameter | 25.4 centimeters |
| Feed Point | 8.9 meters from base (tray 35) |
| Air Injection Point | 1.27 meters from base |
| Number of Trays | 70 |
| Tray Type | Glitsch A-1 valve |
| Tray Spacing | 25.4 centimeters |
| Product draw-off point | Tray 10 |
| Reboiler Type | Shell-Tube thermosiphon |
| Maximum | 150 millimeters mercury absolute |
| Temperatures | |
| Feed | 33° C. |
| Base | 198° C. |
| Middle (Tray 35) | 184° C. |
| Top | 155° C. |
| Reflux | 53° C. |
| Flow Rates | |
| Feed | 22.9 kilograms/hour |
| Air Feed | 420 standard liter/hour |
| Overhead Blowdown | 0.74 kilogram/hour |
| Overhead Water Decant | 0 |
| Residue (acid recycle) | 4.8 kilograms/hour |
| Reflux | 48.5 kilograms/hour |
| Vapor Side Stream Product | 17.43 kilograms/hour |
| Vacuum Vent | 0.88 kilogram/hour |

| Compositions | | | |
|---|---|---|---|
| | Finishing Tower Overhead Wt % | | Vapor Side Stream Product Wt % |
| 2-hexanone | 3.38 | Hexyl hexanoate ester | 0.28 |
| Heptanal | 3.16 | Hexyl 2-methyl Hexanoate ester | 0.05 |
| 2-hexanol | 0.64 | | |
| 1-hexanol | 0.65 | Hexyl heptanoate ester | 0.25 |
| Acetic acid | 2.14 | Gamma heptanolactone | 0.07 |
| Propanoic acid | 0.54 | Hexanoic acid | 0.02 |
| Hexanoic acid | 25.18 | 2-methyl hexanoic acid | 2.07 |
| 2-methyl hexanoic acid | 42.03 | Heptanoic acid | 97.02 |
| Heptanoic acid | 20.80 | Delta heptanolactone | 0.04 |
| Water | 1.48 | Water | 0.02 |

| Conversions, accountabilities and yields | |
|---|---|
| Reactor aldehyde to acid conversion per pass | 71% |
| Reactor oxygen conversion | 84.4% |
| Mass accountability | 101.81% |
| Carbon accountability | 100.37% |
| Oxygen accountability | 99.13% |

-continued

| | |
|---|---|
| Reactor aldehyde to acid yield | 90.6% |
| Overall aldehyde yield to product acid | 86.5% |

The oxygen accountability, reactor aldehyde to acid yield and overall carbon yield to product acid are determined as follows:

$$\% \text{ Oxygen Accountability} = \frac{O(out) - O(VV)}{O(ald) + O(cat) + O(Air)} \times 100$$

O(out) = total moles of oxygen in all unit output streams, moles/hour

O(VV) = total moles of oxygen in vacuum vent streams, moles/hour

O(ald) = total moles of oxygen in the fresh aldehyde feed stream, moles/hour

O(cat) = moles of oxygen (assume all organic as heptanoic acid) in the catalyst addition stream, moles/hour O(air) = moles of oxygen in reactor air feed, moles/hour $$\text{Reactor Aldehyde to Acid Yield } \% = \frac{C(out) - C(cat)}{C(ald)} \times 100$$

C(out) = moles of carbon (from iso and normal heptanoic acid) in all unit output streams, moles/hour C(cat) = moles of carbon (assume all organic as heptanoic acid) in catalyst addition stream, moles/hour C(ald) = moles of carbon (from iso and normal heptanal) in fresh aldehyde feed stream moles/hour Overall Carbon Yield to Product Acid % =

$$\frac{C(VSS) - [C(cat) \times R]}{C(ald)} \times 100$$

C(VSS) = total moles of carbon (from iso and normal heptanoic acid) in vapor side stream and tank surges, moles/hour C(cat) = moles of carbon (assume all organic as heptanoic acid) in catalyst addition stream, moles/hour R = moles of carbon (from iso and normal heptanoic acid) in vapor side stream and Tank surges divided by moles of carbon (from iso and normal heptanoic acid) in all unit output streams C(ald) = moles of carbon (from iso and normal heptanal) in fresh aldehyde feed stream, moles/hour As a comparison of the one stage reactor with recycle alone with a two stage reactor, heptanal is oxidized in the first stage at a conversion of 89–90% of the $C_7$ aldehyde and the first stage reactor product is passed to a second stage reactor where 80% of the remaining aldehyde is oxidized to an overall aldehyde conversion of 97–98%.

The first and second stage reactors were constructed with 316 stainless steel. Their height was 4.57 meters. The diameter of the first stage reactor was 15.25 centimeters and the diameter of the second stage reactor was 10.16 centimeters. The conditions used in these reactors are listed below. The catalyst used in the two stage reactor was not recycled but was removed by mixing the crude oxidation product from the oxidation reactors with aqueous oxalic acid. The insoluble copper and manganese oxalates were precipitated and removed from the organic acid product. The organic acid product was recovered in the heavy ends distillation and finishing distillation equipment depicted in the drawing.

| | |
|---|---|
| First Stage Conditions | |
| Feeds | |
| Aldehyde | 18.1 kilograms/hour |
| Air | 15.55 kilograms/hour |
| Catalyst | 0.54 kilogram/hour |
| Copper | 360 parts per million |
| Manganese | 390 parts per million |
| Reaction Conditions | |
| Air Superficial Velocity | 3.18 centimeters/sec. |
| Unroused Level | 145 centimeters |
| Average Temperature | 58.4° C. |
| Recycle Velocity | 4.2 centimeters/sec. |
| Reactor Pressure | 88 psig |
| Product Analysis | |
| Aldehyde | 11.4 wt % |
| Acid | 77 wt % |
| Catalyst (Cu/Mn) | 360/390 parts per million |
| Vent Analysis | |
| Oxygen | 3.04 mol % |
| Carbon Dioxide | 1.96 mol % |
| Carbon Monoxide | 0.51 mol % |
| Second Stage Conditions | |
| Feeds | |
| First Stage Product | 21.4 kilograms/hour |
| Air | 3.0 kilograms/hour |
| Products | |
| Crude Acid | 21.8 kilograms/hour |
| Vent | 2.52 |
| Reaction Conditions | |
| Air Superficial Velocity | 1.38 centimeters/sec. |
| Unroused Level | 155 centimeters |
| Average Temperature | 57.9° C. |
| Recycle Velocity | 2.3 centimeters/sec. |
| Reactor Pressure | 88 psig |
| Product Analysis | |
| Aldehyde | 2.3 wt % |
| Acid | 88.9 wt % |
| Catalyst (Cu/Mn) | 360/390 parts per million |
| Vent Analysis | |
| Oxygen | 2.73 mol % |
| Carbon Dioxide | 3.77 mol % |
| Carbon Monoxide | 0.18 mol % |
| Reactor aldehyde to $C_7$ acid yield - 87% | |
| Overall aldehyde yield to product $C_7$ acid - 83.5% | |

Comparing the one stage reactor at a lower aldehyde conversion with aldehyde recycle with a two stage reactor with 97–98% conversion, a higher aldehyde to acid yield as well as the overall aldehyde yield to $C_7$ product acid was obtained with the one stage reactor than with the two stage reactor.

What is claimed is:

1. In a process for the separation of an organic saturated aliphatic monocarboxylic acid containing from 5 to 9 carbon atoms from a solution containing said acid, the corresponding aldehyde, manganese and copper, the improvement comprising distilling said acid from said solution in the presence of a sufficient amount of oxygen dispersed in the liquid to prevent copper from plating out on the distillation equipment.

2. The process of claim 1 wherein the organic saturated aliphatic moncarboxylic acid is valeric acid.

3. The process of claim 1 wherein the organic saturated aliphatic monocarboxylic acid is heptanoic acid.

4. The process of claim 1 wherein the organic saturated aliphatic monocarboxylic acid is nonanoic acid.

5. An improved process for producing an organic aliphatic monocarboxylic acid containing 5 to 9 carbon atoms comprising:

(1) oxidizing a saturated aliphatic aldehyde containing 5 to 9 carbon atoms in the presence of a soluble catalyst which is a combination of manganese and copper compounds to form a solution containing unreacted aldehyde, acid product and said catalyst, (2) separating unreacted aldehyde from said solution by distillation in the presence of sufficient oxygen dispersed in the liquid to prevent copper from plating out on the distillation equipment, (3) separating acid product from said catalyst by distillation in the presence of sufficient oxygen to prevent the copper from plating out on the distillation equipment, and (4) recycling recovered unreacted aldehyde to the oxidation step.

6. The process of claim 5 wherein the recovered catalyst is recycled to the oxidation reaction.

7. The process of claim 6 wherein the conversion of aldehyde to acid is maintained in the range from about 70 to about 85 percent.

8. The process of claim 5 wherein valeric acid is produced from valeraldehyde.

9. The process of claim 5 wherein heptanoic acid is produced from heptanal.

10. The process of claim 5 wherein nonanoic acid is produced from nonanal.

11. The process of claim 5 wherein said copper and manganese compounds are cupric acetate and manganous acetate in a molar rati of manganese to copper ranging from about 3:1 to about 1:1 and the total amounts of manganese and copper present each range from about 10 to about 2000 parts per million, based on the total weight of said solution.

12. The process of claim 11 wherein the amounts of cupric and manganous acetate each range from about 200 to about 600 parts per million, based on the total weight of said solution.

13. The process of claim 12 carried out in the presence of an oxygen-containing gas.

14. The process of claim 13 wherein the oxidation reaction is carried out at a pressure ranging from about 20 to about 150 pounds per square inch.

15. The process of claim 14 wherein the oxidation reaction is carried out at a temperature ranging from about 50° C. to about 80° C.

16. The process of claim 15 wherein valeric acid is produced from valeraldehyde.

17. The process of claim 15 wherein heptanoic acid is produced from heptanal.

18. The process of claim 15 wherein nonanoic acid is produced from nonanal.

19. In a process for separating an organic saturated aliphatic monocarboxylic acid from the corresponding aldehyde and an oxidation catalyst comprising copper and manganese, the improvement comprising:

(1) separating unreacted aldehyde from acid product by distillation in the presence of sufficient oxygen to prevent copper from plating out on the distillation equipment, (2) separating acid product from catalyst by distillation in the presence of sufficient oxygen to prevent copper from plating out on the distillation equipment, (3) recycling recovered unreacted aldehyde to the oxidation reaction, and (4) recycling recovered catalyst to the oxidation reaction.

20. The process of claim 19 wherein valeric acid is produced from valeraldehyde.

21. The process of claim 19 wherein heptanoic acid is produced from heptanal.

22. The process of claim 19 wherein nonanoic acid is produced from nonanal.

* * * * *